(12) United States Patent
Condie

(10) Patent No.: US 7,925,344 B2
(45) Date of Patent: Apr. 12, 2011

(54) SYSTEM AND METHOD OF USING AV CONDUCTION TIMING

(75) Inventor: Catherine R. Condie, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 262 days.

(21) Appl. No.: 11/336,753

(22) Filed: Jan. 20, 2006

(65) Prior Publication Data

US 2007/0219589 A1    Sep. 20, 2007

(51) Int. Cl.
*A61N 1/362* (2006.01)
(52) U.S. Cl. .............. 607/9; 600/508; 600/509
(58) Field of Classification Search .......... 607/25, 607/9
See application file for complete search history.

(56) References Cited

U.S. PATENT DOCUMENTS

| | | |
|---|---|---|
| 3,057,356 A | 10/1962 | Greatbatch |
| 3,253,596 A | 5/1966 | Keller |
| 3,478,746 A | 11/1969 | Greatbatch |
| 3,595,242 A | 7/1971 | Berkovits |
| 3,648,707 A | 3/1972 | Greatbatch |
| 3,747,604 A | 7/1973 | Berkovits |
| 4,312,355 A | 1/1982 | Funke |
| 4,386,610 A | 6/1983 | Leckrone |
| 4,428,378 A | 1/1984 | Anderson et al. |
| 4,432,362 A | 2/1984 | Leckrone et al. |
| 4,476,868 A | 10/1984 | Thompson |
| 4,523,593 A | 6/1985 | Rueter et al. |
| 4,577,633 A | 3/1986 | Berkovits et al. |
| 4,587,970 A | 5/1986 | Holley et al. |
| 4,726,380 A | 2/1988 | Vollman et al. |
| 4,727,877 A | 3/1988 | Kallok |
| 4,856,523 A | 8/1989 | Sholder et al. |
| 4,856,524 A | 8/1989 | Baker |
| 4,880,005 A | 11/1989 | Pless et al. |
| 4,890,617 A | 1/1990 | Markowitz et al. |
| 4,932,046 A | 6/1990 | Katz et al. |
| 4,941,471 A | 7/1990 | Mehra |
| 4,953,551 A | 9/1990 | Mehra et al. |
| 5,052,388 A | 10/1991 | Sivula et al. |
| 5,085,215 A | 2/1992 | Nappholz et al. |
| 5,097,832 A | 3/1992 | Buchanan |
| 5,117,824 A | 6/1992 | Keimel et al. |
| 5,133,350 A | 7/1992 | Duffin |
| 5,144,950 A | 9/1992 | Stoop et al. |
| 5,163,427 A | 11/1992 | Keimel |

(Continued)

FOREIGN PATENT DOCUMENTS

EP    0363015    4/1990

(Continued)

OTHER PUBLICATIONS

Jain et al.; "Digoxin, Hyperkalemia, and Kidney Failure", Annals of Emergency Medicine, May 1997, vol. 29, issue 5, pp. 694-697.*

*Primary Examiner* — Niketa I Patel
*Assistant Examiner* — Joseph Stoklosa
(74) *Attorney, Agent, or Firm* — Stephen W. Bauer; Reed A. Duthler

(57) ABSTRACT

In an implantable medical device that provides atrial and ventricular pacing in an atrial-based pacing mode, longer periods of time are permitted for intrinsic AV conduction to occur. By monitoring the patient's AV delay under these circumstances, useful information is obtained that can be correlated to other patient conditions or symptoms.

20 Claims, 5 Drawing Sheets

U.S. PATENT DOCUMENTS

| | | | |
|---|---|---|---|
| 5,188,105 A | 2/1993 | Keimel | |
| 5,188,117 A | 2/1993 | Steinhaus et al. | |
| 5,228,438 A | 7/1993 | Buchanan | |
| 5,273,035 A | 12/1993 | Markowitz et al. | |
| 5,292,340 A | 3/1994 | Crosby et al. | |
| 5,318,594 A | 6/1994 | Limousin et al. | |
| 5,334,220 A | 8/1994 | Sholder | |
| 5,345,362 A | 9/1994 | Winkler | |
| 5,372,607 A | 12/1994 | Stone et al. | |
| 5,388,586 A | 2/1995 | Lee et al. | |
| 5,417,714 A | 5/1995 | Levine et al. | |
| 5,522,859 A | 6/1996 | Stroebel et al. | |
| 5,540,725 A | 7/1996 | Bornzin et al. | |
| 5,584,868 A | 12/1996 | Salo et al. | |
| 5,591,214 A | 1/1997 | Lu | |
| 5,626,623 A | 5/1997 | Kieval et al. | |
| 5,643,326 A | 7/1997 | Weiner et al. | |
| 5,674,257 A | 10/1997 | Stroebel et al. | |
| 5,697,958 A | 12/1997 | Paul et al. | |
| 5,725,561 A | 3/1998 | Stroebel et al. | |
| 5,741,308 A | 4/1998 | Sholder et al. | |
| 5,755,737 A * | 5/1998 | Prieve et al. | 607/4 |
| 5,814,077 A | 9/1998 | Levine et al. | |
| 5,836,974 A | 11/1998 | Christini et al. | |
| 5,861,007 A | 1/1999 | Hess et al. | |
| 5,873,895 A | 2/1999 | Sholder et al. | |
| 5,954,755 A | 9/1999 | Casavant | |
| 5,999,850 A | 12/1999 | Dawson et al. | |
| 6,045,513 A * | 4/2000 | Stone et al. | 600/508 |
| 6,058,326 A | 5/2000 | Hess et al. | |
| 6,122,546 A | 9/2000 | Levine et al. | |
| 6,128,529 A | 10/2000 | Esler et al. | |
| 6,128,534 A | 10/2000 | Park et al. | |
| 6,141,586 A | 10/2000 | Mower | |
| 6,169,918 B1 | 1/2001 | Haefner et al. | |
| 6,198,968 B1 | 3/2001 | Prutchi et al. | |
| 6,256,541 B1 | 7/2001 | Heil et al. | |
| 6,321,115 B1 | 11/2001 | Mouchawar et al. | |
| 6,397,105 B1 | 5/2002 | Bouhour et al. | |
| 6,434,424 B1 | 8/2002 | Igel et al. | |
| 6,477,416 B1 | 11/2002 | Florio et al. | |
| 6,609,028 B2 | 8/2003 | Struble | |
| 6,654,637 B2 | 11/2003 | Rouw et al. | |
| 6,697,673 B1 | 2/2004 | Lu | |
| 6,731,980 B1 | 5/2004 | Mouchawar et al. | |
| 6,772,005 B2 | 8/2004 | Casavant et al. | |
| 6,792,307 B1 | 9/2004 | Levine et al. | |
| 6,873,875 B1 | 3/2005 | Gilkerson et al. | |
| 6,904,315 B2 | 6/2005 | Panken et al. | |
| 6,925,326 B1 | 8/2005 | Levine et al. | |
| 6,978,175 B1 | 12/2005 | Florio et al. | |
| 7,027,868 B2 | 4/2006 | Rueter et al. | |
| 7,123,960 B2 | 10/2006 | Ding et al. | |
| 7,130,683 B2 | 10/2006 | Casavant et al. | |
| 7,218,965 B2 | 5/2007 | Casavant et al. | |
| 7,245,966 B2 | 7/2007 | Betzold et al. | |
| 7,248,924 B2 | 7/2007 | Casavant | |
| 7,254,441 B2 | 8/2007 | Stroebel | |
| 7,283,872 B2 | 10/2007 | Boute et al. | |
| 2002/0038482 A1 | 4/2002 | Mennicke et al. | |
| 2002/0041700 A1 | 4/2002 | Therbaud | |
| 2002/0062139 A1 * | 5/2002 | Ding | 607/25 |
| 2002/0082646 A1 | 6/2002 | Casavant et al. | |
| 2002/0128687 A1 | 9/2002 | Baker et al. | |
| 2002/0138417 A1 | 9/2002 | Lawrence | |
| 2003/0078627 A1 * | 4/2003 | Casavant et al. | 607/9 |
| 2004/0010292 A1 | 1/2004 | Amblard et al. | |
| 2004/0024694 A1 | 2/2004 | Lawrence et al. | |
| 2004/0078321 A1 | 4/2004 | Lawrence | |
| 2004/0117316 A1 | 6/2004 | Gillum | |
| 2004/0162466 A1 * | 8/2004 | Quy | 600/300 |
| 2004/0260349 A1 * | 12/2004 | Stroebel | 607/9 |
| 2005/0038482 A1 | 2/2005 | Yonce et al. | |
| 2005/0055059 A1 | 3/2005 | Betzold et al. | |
| 2005/0096708 A1 | 5/2005 | Seim et al. | |
| 2005/0177197 A1 | 8/2005 | Betzold | |
| 2005/0267539 A1 | 12/2005 | Betzold et al. | |
| 2005/0273430 A1 | 12/2005 | Pliha | |
| 2007/0203523 A1 | 8/2007 | Betzold | |
| 2007/0213777 A1 | 9/2007 | Betzold et al. | |

FOREIGN PATENT DOCUMENTS

| | | |
|---|---|---|
| EP | 0448193 | 9/1991 |
| EP | 0624386 | 11/1994 |
| EP | 0830877 | 3/1998 |
| EP | 1449562 | 8/2004 |
| WO | WO 95/32758 | 12/1995 |
| WO | WO 02/051499 | 7/2002 |
| WO | WO 2005/097259 | 10/2005 |
| WO | WO 2005/113065 | 12/2005 |
| WO | WO 2006/079037 | 7/2006 |
| WO | WO 2006/079066 | 7/2006 |

* cited by examiner

SYSTEM AND METHOD OF USING AV CONDUCTION TIMING

BACKGROUND

1. Field of the Invention

The present invention relates to implantable medical devices and, more specifically, to medical devices that provide data to clinicians for analysis.

2. Description of the Related Art

There are numerous types of implantable medical devices (IMDs) that are available for gathering information and/or delivering therapy. In the cardiac arena, pacemakers (implantable pulse generators (IPGs)) and implantable cardioverter/defibrillators (ICDs) are the most common, and it should be appreciated that ICDs often also include pacing capabilities. The assignee of the present invention also makes an implantable loop recorder (ILM) that does not deliver any electrical therapy, but does monitor and record various cardiac signals. The IMDs will have a memory unit that stores certain types of information and transmits that information to an external device through a telemetry session for use and analysis.

When an IMD has pacing capabilities, that device is programmed to operate in a given mode. For example, a commonly used mode is referred to as DDD/R. This means that the IMD can sense and pace in multiple chambers of the heart (typically, the right atrium and right ventricle) and is rate responsive. The DDD/R mode is very comprehensive and provides for almost complete control of cardiac timing. After each atrial event (either intrinsic or paced), an AV interval (AVI) is started. At the end of the AVI, the device will deliver a ventricular pacing pulse, unless one has occurred intrinsically. However, since the DDD/R mode is comprehensive and attempts to provide a normalized cardiac cycle, the AVI is relatively short; thus, this almost always results in a ventricular pacing pulse occuring. In other words, a patient would need to have unusually fast intrinsic conduction time to have intrinsic ventricular depolarization when operating in a nominal DDD/R mode.

While the DDD/R mode is comprehensive and beneficial, there is a class of patients that have intact but "slow" AV conduction times. Thus, but for the setting of the AVI, the atrial event would naturally lead to the depolarization of the ventricles without having to provide ventricular pacing. There has been a recent recognition that allowing intrinsic conduction, even at longer intervals, is preferred to providing ventricular pacing. There are, of course, reasons why such pacing would be preferable or necessary. For example, a patient having complete heart block would be dependent upon ventricular pacing. Certain therapies, such as cardiac resynchronization therapy (CRT), pace both the left and right ventricles for heart failure patients.

As indicated, the recognition that ventricular pacing, particularly pacing in the right ventricular apex, is less desirable than permitting intrinsic conduction, is relatively recent. The assignee of the present invention has developed a mode that facilitates intrinsic conduction while providing ventricular pacing only when necessary. One commercial embodiment of this mode is referred to as the Managed Ventricular Pacing™ mode or the MVP™ mode. In this mode, a full cardiac cycle is permitted to elapse without providing ventricular pacing. Thus, for a given cycle, this affords the maximum amount of time for intrinsic conduction to occur. If no ventricular activity occurs in a given cycle, pacing is provided in the subsequent cycle; and, if this occurs too frequently (e.g., 2 out 4 cycles), then ventricular pacing in a standard mode (e.g., DDD/R) is provided for a period of time. Periodic conduction checks are performed to determine if intrinsic conduction has returned, as such block is often transient in patients. This discussion is meant to be exemplary and illustrative and in no way limiting of the MVP™ mode or other modes.

There are other modes that seek to extend or maximize duration during which intrinsic conduction is permitted. Some of these modes do not permit a complete cardiac cycle to transpire without ventricular activity, but provide the longest permissible AV interval such that a delivered ventricular pace will not adversely interfere with the subsequent atrial event (from a timing perspective). As used herein, these modes are collectively referred to as atrial-based pacing mode. In short, atrial-based pacing modes utilize A-A intervals to determine and/or control cardiac rate and seek to limit ventricular pacing by either tolerating a cycle devoid of ventricular activity or providing a relatively long AV interval as compared with standard DDD modes.

With atrial-based pacing, the atrial rate is known or knowable, but the actual AV delay is generally not known for a given cycle, as intrinsic conduction can occur at various times. The maximum variability occurs in modes that tolerate an absence of ventricular activity for a given cycle, as the actual AV delay may be equal to or any value less than the A-A interval, or there may not be a value for a given cycle. Comparing this to standard DDD/R timing, a typical AVI may be on the order of 150 ms, as an example. Thus, the AV delay could be 0-150 ms and, in practice, very short delays are likely to be PVCs, and thus, the range is 80-150 ms. In an atrial-based mode tolerating absent ventricular cycles, at a rate of 60 bpm, the AV delay may be 0-1000 ms. Thus, in atrial-based pacing modes the range of timing is greatly expanded.

DETAILED DESCRIPTION

Figure 1:
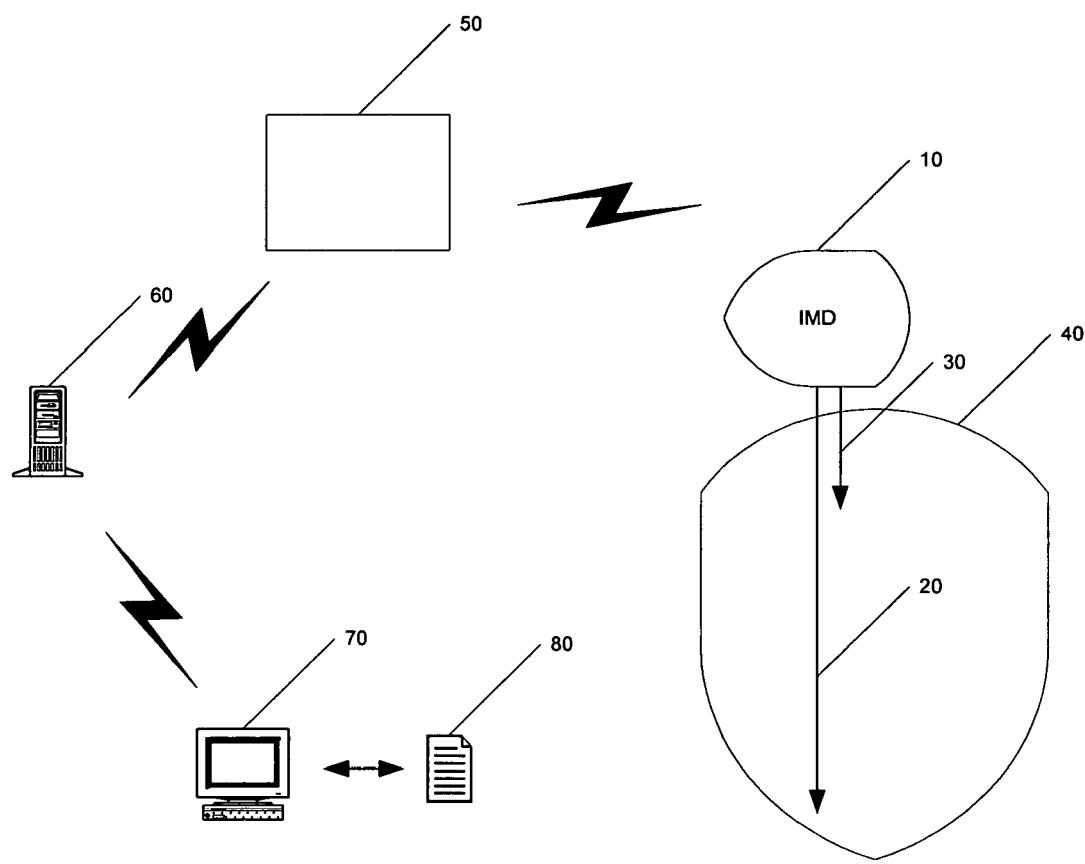
FIG. 1 is a schematic diagram of a system consistent with the teachings of the present invention.

FIG. 1 is a schematic illustration of an exemplary system consistent with the teachings of the present invention. An implantable medical device (IMD) 10 is illustrated having two leads—an atrial lead 30 and a ventricular lead 40—that may be implanted within a heart 40. Additional leads may be employed and the housing of the IMD 10 may serve as an electrode. Each lead 20, 30 senses electrical activity within the heart 40 and is capable of delivering pacing pulses. The components of the IMD 10 are generally well known and not separately illustrated. These components would typically include, without limitation, a microprocessor, memory, battery, capacitor and a telemetry module.

The IMD 10 provides data to and/or receives information from an external medical device (EMD) 50. EMD 50 may be a medical device programmer, an in-home monitor or a personal communication device such as a wireless phone, pager, or the like. As illustrated, the EMD 50 serves to communicate with the IMD 10 and transmit information to a remote server 60, such as the Medtronic CareLink™ Network. Information from the server 60 may then be accessed at a user's computing device 70, and information 80 from and about the IMD 10 is displayed and/or printed. In the case of a medical device programmer or a device reader, one- or two-way communication with the IMD 10 may occur without subsequent communication from the EMD 50 to another device and the information 80 could be displayed on or obtained from the EMD 50.

As discussed, the IMD 10 is operable in an atrial-based pacing mode. That is, atrial pacing is provided as needed; however, ventricular pacing is reduced or minimized. In other words, the patient's natural conduction is permitted to depolarize the ventricles, despite what may normally be considered "long" AV delays. As both atrial and ventricular activity is sensed, the resultant timing is known. Thus, AV delays are measured and stored in the memory of the IMD 10. This data may be telemetered out and analyzed as discussed herein.

Figure 2:
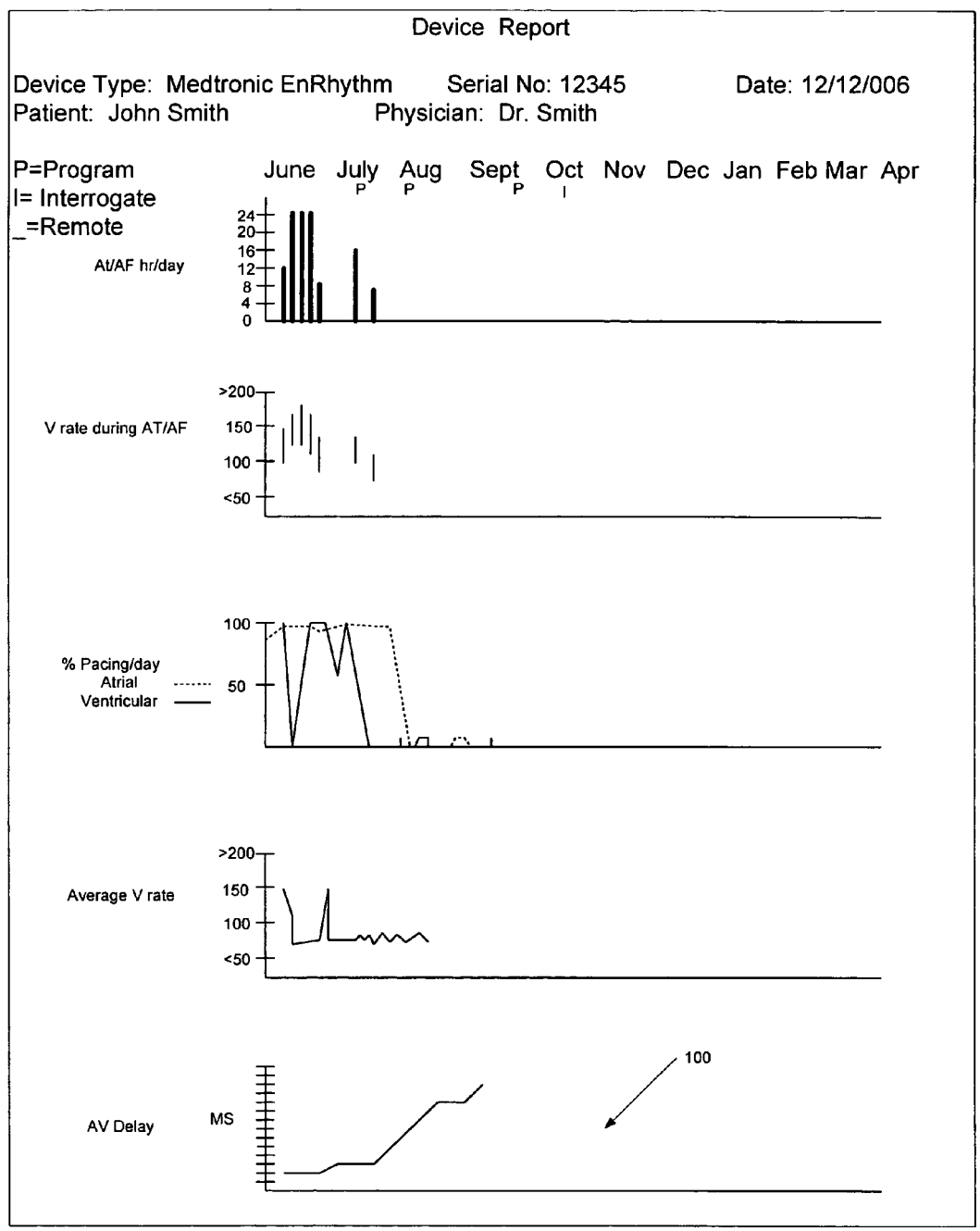
FIGS. 2-3 illustrate various exemplary device reports.

FIG. 2 is an exemplary device report 80 that may take any appropriate form, such as a printed report or displayed electronic document. It should be appreciated that the content, form, and arrangement of report 80 are non-limiting and merely illustrative of how various types of information may be provided to a physician or caregiver to aid in managing a disease state of a patient. It should be further appreciated that other types of information obtained from IMD 10, other sensors, patient input, or other electronic- or manually-accessed medical records could be provided in context. Thus, the most relevant information to a particular type of caregiver is selected and presented in report 80.

Various sample data sets are provided, such as how much AT/AF occurs in a given day, the ventricular rate during these events, percentage of pacing and an average ventricular rate. These data sets simply illustrate various cardiac parameters that can be represented in graphical form over time and do not represent actual or even correlated data.

Data subset 100 is a graph that illustrates the patient's AV delay in milliseconds (Y axis) over time (X axis). Such data is relevant, assuming the patient does not have complete heart block (e.g., is pacemaker dependent) and is operating in an atrial-based pacing mode so that the intrinsic conduction timing is permitted to emerge. As used herein, the AV delay is relevant over a consistent heart rate. That is, as heart rate changes, the AV delay is expected to change. Thus, the data subset 100 is provided for a given heart rate or rate range. Though not shown, similar data may be provided for multiple rates or rate ranges.

As indicated, the AV delay data is presented for a given heart rate.

Multiple values for different heart rates may be collected and displayed.

This will tend to illustrate conditions that are more prevalent at specific heart rates. As the patient's heart rate fluctuates normally, it may be difficult to obtain measurements at a specific predetermined value. Thus, the IMD 10 can be programmed to pace at the desired rate at a given interval (e.g., four times per day at 60 bpm) for a sufficiently long period of time such that the underlying conduction emerges. Naturally, the test would be postponed or cancelled based upon patient need. For example, if the patient is strenuously exercising, the IMD 10 will not alter the heart-rate from, e.g., 130 bpm to 60 bpm, simply for data collection.

Furthermore, the activity sensor may be utilized to determine periods of rest and/or sleep. This determination may be used to identify time to pace at specific rates. Alternatively, rather than forcing a specific rate, the rate may be noted and data collected at the resting rate.

Trending of AV delay data 100 can illustrate various aspects of the patient's condition. Assuming the patient is generally healthy, the AV delay should remain relatively constant (with normal fluctuations for variation due to rate being normal). Patients may experience period of intermittent heart block and this will be represented as the device delivers ventricular pacing. Assuming the frequency of such occurrences is tolerable, the caregiver may deem the condition acceptable.

Figure 3:
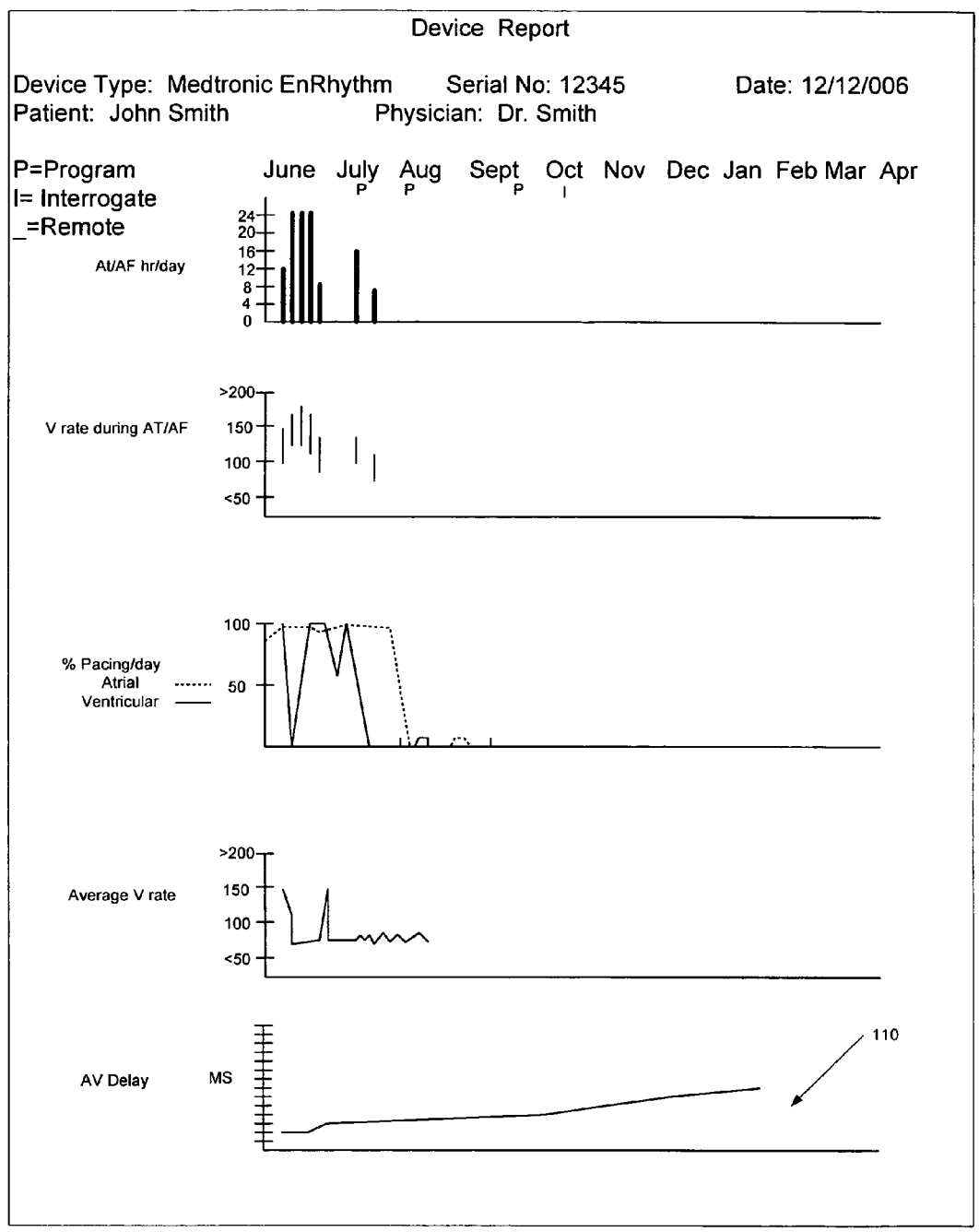

FIGS. 2 and 3 illustrate two AV delay graphs 100, 110 illustrative of changing AV delays. In FIG. 3, graph 110 illustrates a gradual upward progression of AV delays. This would likely be indicative of the natural, worsening progression of AV nodal disease. Assuming everything else remains constant, a longer AV delay will result in a shorter VA delay; in other words, the ventricular event is relatively close or becomes closer in time to the subsequent atrial event. By noting this, the caregiver may make certain decisions as to whether to treat this condition or simply be aware of the likely outcome. For example, such progression may result in complete heart block. While the atrial-based pacing modes will operate properly, the caregiver may have a preference to utilize a different mode. Similarly, the AV delay may reach a duration wherein a given atrial-based pacing mode will tolerate the timing, but the caregiver or patient may prefer to select a different pacing mode. Of course, the IMD 10 may be programmed to make such a mode switch based upon the trending data itself. That is, if the AV delay reaches a predetermined threshold, then the device switches to e.g., DDD/R. A variety of parameters may be used by the device, such as the actual duration of the AV delay(s), the length of time the patient averages such delays, or the slope of the change in AV delays (that is, the rate of change or other predetermined criteria). As one example, the IMD 10 may determine to switch to DDD/R if the average AV delay exceeds 400 ms for X number of days.

FIG. 2 illustrates an AV delay graph 100 wherein the change in AV delay over time is more rapid. A more rapid change may be indicative of various conditions that, when alerted to, the caregiver and/or patient may take various actions to manage the patient's disease. It should be appreciated that the example graph of FIG. 2 represents data over a period of months. A rapid change could occur over a much shorter period of time and be similarly represented with an appropriate time scale. For example, the change could occur over a matter of a few hours or a few days. The data is collected and presented in the same fashion. Furthermore, with regularly scheduled patient follow-up visits (in-office or remote) typically occuring once per quarter, such a change may be cause for the IMD 10 or the EMD 50 to initiate a communication session so that the caregiver is provided with the data in a timely manner.

As indicated, normal progression of AV nodal sickness is gradual over time. More rapid increases and/frequent changes to AV delay is indicative of other issues for the patient. Specifically, what those issues are will vary, and may be determined from the context provided by additional information accessible to the caregiver. For example, the device report 80 may include other cardiac data that provides the appropriate contextual information. Other information, in context, may be provided by alternative mechanisms. For example, the patient's medical record may be reviewed, the electronic medical record (EMR) may be delivered, the device report 80 may be modified to include information from the EMR, and of course, the caregiver may have their own knowledge of the patient from which to draw upon. The mechanism for providing information in context for disease management is described in co-pending applications (U.S. patent application Ser. No. 11/038,814 filed Jan. 20, 2005; and U.S. patent application Ser. No. 11/038,835 filed Jan. 20, 2005), which are herein incorporated by reference in their entirety. Thus, what the AV delay trends indicate is not meant to be a limiting factor of the present invention.

With the data provided, the caregiver can evaluate the AV delay information and determine if there is a cyclic correlation between the changes and other events. For example, the patient might experience prolonged AV delays after delivery of therapy for ventricular tachycardia. The caregiver could determine if this is a concern and, if so, the IMD 10 could be programmed to operate in a standard mode for a corresponding period of time after such therapy is delivered.

A patient's balance or level of electrolytes is known to affect AV delays. Thus, the caregiver may determine that the changes in AV delay represent an imbalance in electrolytes with potential causes including dehydration, diabetes, and the effects of various medications. Thus, the patient may be advised to consume fluids, manage their diabetes through dietary or medicinal modifications (or simply to follow their prescribed regime if not doing so diligently), or titrating or replacing the various medications. Patients having renal disease often have dialysis as a treatment. Changes in the AV delay may be associated with the effectiveness of this treatment and the state of the disease. Thus, AV delay data may be an indication that, for example, dialysis should occur more frequently. Another condition affecting AV delay is infarction occuring in certain areas of the heart. Thus, the AV delay data may lead the caregiver to investigate this as an issue. Furthermore, the AV delay data may be correlated to patient complaints of angina, which would further suggest an infarct. Lyme disease has been known in certain circumstances to affect AV delay. Acute changes in blood pressure can lead to conduction irregularities. Thus, the AV delay data may be correlated to such pressure fluctuation (which may otherwise be unmeasured). The hypertension may then be treated; alternatively, acute hypertension may be caused by arterial insult or injury, including obstructions. Thus, these potentially serious matters may be diagnosed after the initial AV delay data indicates that issues are present. In other words, the AV delay data may in and of itself permit a caregiver to diagnose a condition and prescribe a therapy or corrective action; the AV delay data combined with other data in context may provide the same result; and the AV delay data may indicate that an issue exists that is undeterminable from the current data, which leads the caregiver to investigate further. Once again, these examples are not meant to be limiting.

Another use of the AV delay trend data set is as a correlative trigger for data collection. Implantable medical devices have limited memory capacity. Thus, certain devices may not be able to record complete data sets for extended periods of time. These devices sometime include an external patient activator. When the patient has specific symptoms, they utilize the activator, which causes the IMD to record the relevant data set for the time period including the patient-indicated symptoms. In some cases, the patient may not perceive any symptoms when a particular condition is occurring or may be unable to utilize the activator, either because they are physically unable, or simply do not have the activator with them. Thus, the AV delay data may correlate to the conditions of interest to the caregiver. As such, when the AV delay reaches a particular level or varies at a particular rate of change (e.g., slope) then the IMD is triggered to store additional data.

As used herein, the AV delay refers to the interval between any atrial event and any ventricular event. The data is only meaningful if the ventricular events are generally intrinsic. That is, a certain number of ventricular pacing pulses (fixed AV interval) will still result in useful averaged data; however, if pacing continuously in the ventricles, this data loses its value. As such, the IMD 10 may exclude data resulting from a ventricular pace. Alternatively, such data may be included with or without specifically identifying its effect on the average. Similarly, the AV delay data may be presented as a combination or split between events triggered from an atrial pace (Ap-Vs) and events triggered from intrinsic atrial depolarization (As-Vs). As one can appreciate, such data may be presented to a user in any number of formats.

Figure 4:
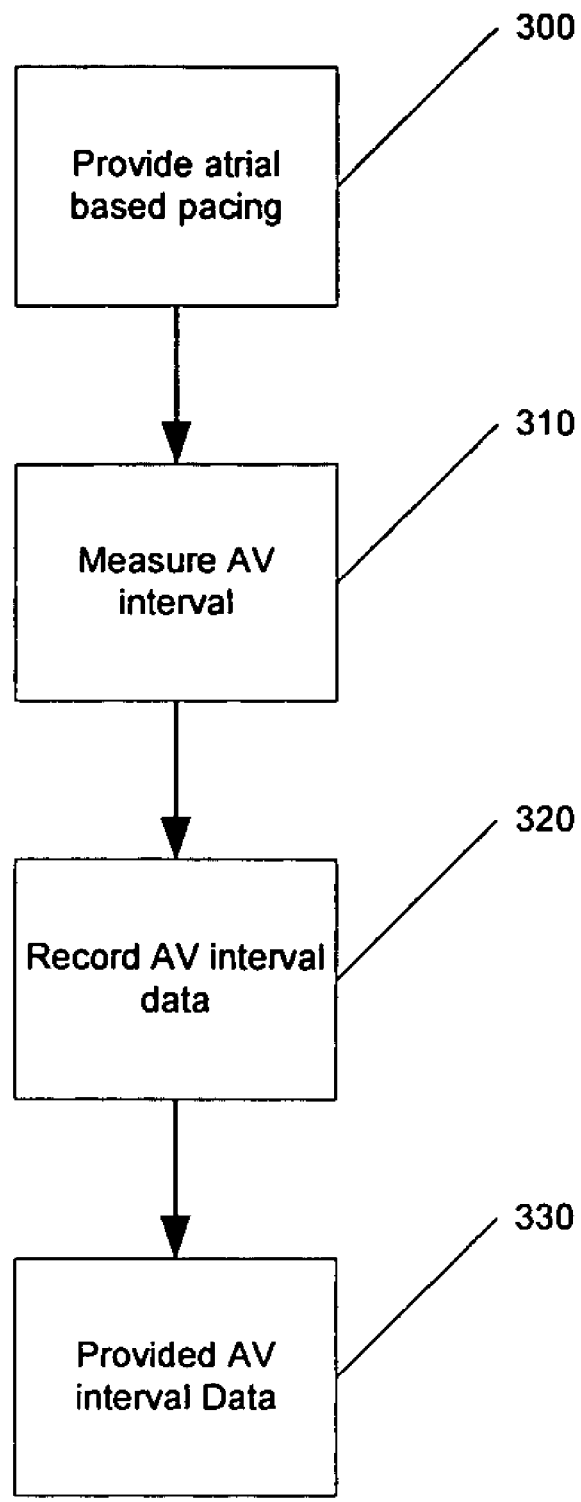
FIGS. 4-5 are flow charts of processes consistent with the teaching of the present invention.

FIG. 4 is a flowchart illustrating a method consistent with the teachings of the present invention. At step 300, the IMD 10 begins to operate in an atrial-based pacing mode. As this provides for rhythm control based upon atrial timing (A-A) intervals, either paced or sensed, this parameter is known. In the absence of heart block, the atrial-based pacing mode provides a relatively long time for intrinsic conduction to occur; this window may even equal the A-A interval. Thus, the timing of the intrinsic ventricular event is unknown, but when an intrinsic ventricular event occurs, it is sensed and AV delay is measured (310) and recorded (320). If no intrinsic ventricular event is sensed, then the IMD 10 operates according to the protocols of the atrial-based pacing mode (e.g., providing a ventricular pacing pulse in the subsequent cardiac cycle). The collected data is then provided (330). The data may be provided to or through an EMD 50 and ultimately in a device report 80; or may be used by the IMD 10 or EMD 50 to take specific action, such as recording data based upon the AV delay measurements.

Figure 5:
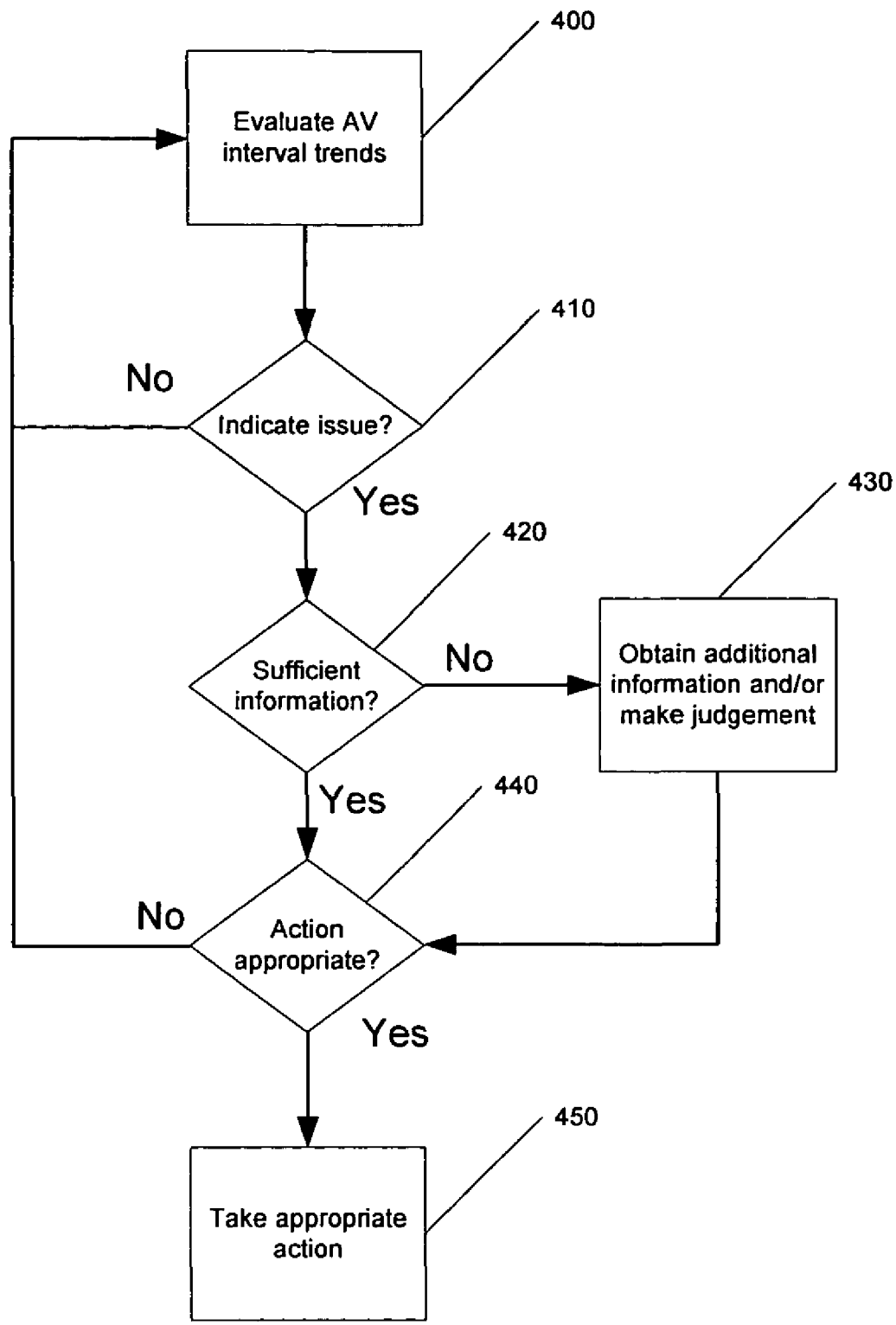

The AV delay data is presented in an appropriate form to a caregiver who evaluates (400) the data, as indicated in FIG. 5. This step would also include any automated analysis of the data performed by the IMD 10, the EMD 50, the server 60 and would also include the incorporation of any other contextual data obtained from the patient or patient records. The caregiver determines (410) whether the AV delay data is indicative of potential issues. This step may be performed for several different reasons. In one case, the data is reviewed during a normal device check (e.g., monthly, quarterly, etc.) where no issue has been raised to cause the caregiver to seek the data. In another case, the IMD 10, EMD 50, or patient has raised a concern and the data has been submitted to the caregiver for this reason. In other words, the caregiver is alerted to a potential issue and is reviewing the data because of that issue. Similarly, once an issue has been raised, the caregiver may evaluate these trends more frequently to monitor the issue. For example, the patient may be taking a medication that needs frequent titration. The AV delay may indicate when the medication should be titrated; thus, the caregiver obtains and monitors this data frequently for this issue, as opposed to just regularly-scheduled, relatively infrequent device checks.

Of course, some conditions monitored may require infrequent review;

thus, this becomes a factor to consider with each such scheduled device check but might not warrant an increase in the frequency of monitoring or data collection.

When the AV delay data is evaluated (400), the caregiver determines if any issue is raised by the data (410). If not, the process returns and the caregiver re-evaluates the data (400) at the next appropriate time interval. Conversely, if the data does indicate that an issue exists, the caregiver determines if he or she has sufficient information to evaluate and act upon the data (420). If there is insufficient data, the caregiver will obtain additional information and/or make an evaluation based upon their medical judgment (430). Such additional information may be obtained from journals and databases, patient records, or patient communication. Furthermore, the data itself may be insufficient and require additional evaluation and/or testing of the patient, which may be scheduled and performed.

Once the caregiver has diagnosed the patient, the caregiver determines if there is an appropriate course of action (440). In some cases, no action is required or available; thus, the process reverts to step 400 and the data continues to be monitored. If an appropriate course of action is identified (440), that action is then performed (450). As indicated, such actions may include adjusting device parameters, titrating medication, prescribing medication, eliminating the use of a medication, adjusting diet or other patient behavior, increasing/modifying dialysis, modifying the parameters of another medical device (e.g., insulin drug pump, CPAP machine), or performing other medical procedures (e.g., bypass operation, stent implantation).

Thus, AV delay data is monitored and provided to a caregiver; The trending of this data over short or long periods of time may be indicative of various patient conditions when an atrial-based pacing mode is selected. The selection of an atrial-based pacing mode provides a sufficient time window for intrinsic conduction to occur and provide meaningful data, which would otherwise be unavailable with predefined nominal AV pacing intervals such as those used in the DDD/R mode.

The invention claimed is:

1. A system comprising:
   means for providing cardiac pacing;
   means for controlling the means for providing cardiac pacing according to an atrial-based pacing mode, wherein the atrial-based pacing mode provides multiple-beat AV coordination and minimizes ventricular pacing by tolerating a complete cardiac cycle devoid of ventricular activity while maintaining AV synchrony, wherein the pacing mode utilizes an A-A interval to determine the cardiac cycle;
   means for collecting data indicative of a time interval for atrial-ventricular conduction delay (AV delay);
   means for correlating the collected data with a trigger condition to determine whether to initiate collection of data related to patient-indicated symptoms, wherein the trigger condition is determined based on the collected data; and
   means for displaying the collected data.

2. The system of claim 1, wherein the means for displaying further comprise means for displaying a trend of AV delay over time.

3. The system of claim 1, further comprising:
   means for transmitting the collected data from the means for providing cardiac pacing;
   means for receiving the transmitted data and formatting the transmitted data; and
   means for accessing the formatted data.

4. The system of claim 3, further comprising means for correlating the data to a medical condition.

5. The system of claim 4, further comprising means for delivering a therapy based upon the correlated medical condition.

6. The system of claim 5, wherein the means for delivering a therapy includes changing pacing parameters.

7. The system of claim 5, wherein the means for delivering a therapy includes means for titrating a medication.

8. The system of claim 5, wherein the means for delivering a therapy includes changing a frequency of dialysis.

9. The system of claim 1, further comprising means for analyzing the collected data to determine whether a trend is present and means for comparing the trend to the trigger condition.

10. A method comprising:
    providing cardiac pacing with a device operating in an atrial-based pacing mode, wherein the atrial-based pacing mode permits an entire cardiac cycle to pass without ventricular activity with ventricular pacing provided in a cycle immediately subsequent to the cycle without ventricular activity, wherein the pacing mode utilizes an A-A interval to determine the cardiac cycle;
    measuring an atrial ventricular conduction delay (AV delay) for each of a plurality of cardiac cycles;
    storing the measured AV delays;
    transmitting the stored AV delays to an external device as AV delay data;
    using the AV delay data to evaluate a medical status; and
    correlating the measured AV delays with a trigger condition to determine whether to initiate collection of data related to patient-indicated symptoms.

11. The method of claim 10, further comprising:
    providing the AV delay data to a central server;
    formatting the AV delay data; and
    providing the formatted AV delay data on a device report.

12. The method of claim 11, further comprising:
    accessing the central server from a remote computer; and
    receiving the device report at the remote computer and using the device report to evaluate the medical status.

13. The method of claim 11 wherein formatting the AV delay data includes providing a graphical representation of the AV delay data over a time period.

14. The method of claim 10, wherein using the AV delay data to evaluate a medical condition further includes providing a therapy based upon the evaluation.

15. The method of claim 14, wherein the providing of the therapy includes modifying a pacing parameter.

16. The method of claim 14, wherein the providing of the therapy includes prescribing a medication.

17. The method of claim 14, wherein the providing of the therapy includes titrating a drug.

18. The method of claim 14, wherein the providing of the therapy includes modifying a frequency of dialysis.

19. The method of claim 10, wherein the evaluating of the medical status includes conducting additional physical examination of a patient based upon the AV delay data.

20. The method of claim 10, further comprising analyzing the measured AV delays and triggering a detailed data recording session based upon the measured AV delays.

* * * * *